US012565465B2

(12) United States Patent
Evans et al.

(10) Patent No.: US 12,565,465 B2
(45) Date of Patent: Mar. 3, 2026

(54) PROCESS FOR FORMALDEHYDE MANUFACTURE

(71) Applicant: Johnson Matthey Davy Technologies Limited, London (GB)

(72) Inventors: Gary Evans, Reading (GB); Robert Häggblad, Perstorp (SE); Kaisa Kisko, Perstorp (SE)

(73) Assignee: Johnson Matthey Davy Technologies Limited, London (GB)

( * ) Notice: Subject to any disclaimer, the term of this patent is extended or adjusted under 35 U.S.C. 154(b) by 461 days.

(21) Appl. No.: 18/040,738

(22) PCT Filed: Oct. 13, 2021

(86) PCT No.: PCT/GB2021/052647
§ 371 (c)(1),
(2) Date: Feb. 6, 2023

(87) PCT Pub. No.: WO2022/079434
PCT Pub. Date: May 21, 2022

(65) Prior Publication Data
US 2023/0271910 A1 Aug. 31, 2023

(30) Foreign Application Priority Data
Oct. 13, 2020 (GB) ..................................... 2016230

(51) Int. Cl.
*C07C 45/38* (2006.01)

(52) U.S. Cl.
CPC ........ *C07C 45/38* (2013.01); *C07C 2523/881* (2013.01)

(58) Field of Classification Search
CPC .......................... C07C 45/38; C07C 2523/881
See application file for complete search history.

(56) References Cited

U.S. PATENT DOCUMENTS

| 2,504,402 | A | 4/1950 | Du Pont |
| 6,037,290 | A | 3/2000 | Wachs et al. |
| 7,381,851 | B2 | 6/2008 | Olbert et al. |
| 8,877,966 | B2 | 11/2014 | Herzog et al. |
| 9,120,743 | B2 | 9/2015 | Peterson et al. |
| 2012/0071688 | A1 | 3/2012 | Herzog et al. |
| 2018/0148399 | A1 | 5/2018 | Holmberg |
| 2020/0276537 | A1 | 9/2020 | Boman |

FOREIGN PATENT DOCUMENTS

| BG | 97983 | A | 2/1995 |
| CN | 105392766 | A | 3/2016 |
| CN | 106552658 | A | 4/2017 |
| CN | 107556175 | A | 1/2018 |
| CN | 111094885 | A | 5/2020 |
| CN | 107624109 | B | 8/2021 |
| DE | 102009014541 | A1 | 9/2010 |
| EP | 1 699 551 | A1 | 9/2006 |
| EP | 2 213 370 | A2 | 8/2010 |
| EP | 2 303 821 | A1 | 4/2011 |
| EP | 2 310 348 | A2 | 4/2011 |
| EP | 2 349 968 | A2 | 8/2011 |
| EP | 2 355 925 | A1 | 8/2011 |
| EP | 3 288 917 | A1 | 3/2018 |
| FR | 870705 | A | 3/1942 |
| FR | 1 213 075 | A | 3/1960 |
| GB | 647743 | A | 9/1942 |
| GB | 2569917 | A | 7/2019 |
| WO | 9632189 | A1 | 10/1996 |
| WO | 99/52629 | A1 | 10/1999 |
| WO | 02/22540 | A2 | 3/2002 |
| WO | 2005/063375 | A1 | 7/2005 |
| WO | 2009/156655 | A1 | 12/2009 |
| WO | 2010/010287 | A2 | 1/2010 |
| WO | 2010/034480 | A2 | 4/2010 |
| WO | 2010/046110 | A1 | 4/2010 |
| WO | 2014/70735 | A1 | 5/2014 |
| WO | 2016/177999 | A1 | 11/2016 |

OTHER PUBLICATIONS

Soederhjelm, et al., "On the Synergy Effect in MoO3—Fe2(MoO4)3 Catalysts for Methanol Oxidation to Formaldehyde," Top Catal (2008) 50:145-155.

*Primary Examiner* — Sikarl A Witherspoon
(74) *Attorney, Agent, or Firm* — BakerHostetler

(57) ABSTRACT

A process for the production of formaldehyde from methanol comprising the steps of: feeding to a reactor a feed stream comprising the methanol and an oxygen-containing gas; reacting the methanol in the gas phase with the oxygen-containing gas in the reactor in the presence of a catalyst comprising oxides of iron and molybdenum; and recovering a formaldehyde reactor outlet stream from the reactor, the formaldehyde reactor outlet stream comprising formaldehyde and carbon monoxide. The catalyst comprises copper in an amount of at least 0.025 wt %, or at least 0.05 wt %, of the catalyst and in that the molar ratio of carbon monoxide to formaldehyde in the formaldehyde reactor outlet stream is at least 5% less than the molar ratio of carbon monoxide to formaldehyde in the formaldehyde reactor outlet stream in the same process using a catalyst containing essentially no copper.

18 Claims, 4 Drawing Sheets

PROCESS FOR FORMALDEHYDE MANUFACTURE

FIELD OF THE INVENTION

The invention concerns a process, in particular for the oxidation of methanol to produce formaldehyde.

BACKGROUND

Processes for the manufacture of formaldehyde in which methanol is oxidised over a catalyst have been well-known for many years. One well-known process includes the oxidation of methanol over a mixed oxide catalyst, usually containing oxides of iron and molybdenum: $CH_3OH+0.5 O_2 \rightarrow CH_2O+H_2O$. Plants operating this process usually operate at a reactor inlet pressure of about 1 barg or less. Although it would be desirable to increase the production from a plant by increasing the pressure at which the process is operated, this can result in problems due to a loss in selectivity of the catalyst. The result is an increase in formation of unwanted by-products. One such by-product is dimethyl ether (DME), believed to be formed from an increase in the concentration of methoxy groups adsorbed onto the catalyst surface:

$$2CH_3OH \rightarrow CH_3OCH_3+H_2O.$$

Another possible by-product is carbon monoxide, which is formed by the reaction of formaldehyde and oxygen:

$$CH_2O+\tfrac{1}{2}O_2 \rightarrow CO+H_2O.$$

The loss of formaldehyde resulting from the production of carbon monoxide can be quantified as the 'CO loss', which is defined as the molar ratio of carbon monoxide to formaldehyde in the reactor effluent. In a typical process, a CO loss of about 4% to about 6% (i.e. a molar ratio of carbon monoxide to formaldehyde of about 4%, or 1:25) is expected. It would be desirable to reduce the CO loss so as to increase the formaldehyde yield and hence increase the profitability of the process for an operator.

Another possible by-product is methyl formate which is formed according to the reactions:

$$2CH_3OH+O_2 \rightarrow HCOOCH_3+H_2O$$

$$2HCHO \rightarrow HCOOCH_3$$

$$HCOOH+CH_3OH \leftrightarrow HCOOCH_3+H_2O$$

It would be desirable to reduce the methyl formate because this also reduces the formaldehyde yield and profitability of the operator and leads to the production of formic acid, according to the equilibrium reaction above, which is problematic for producers of adhesives and urea formaldehyde and necessitates the addition of buffers to the formalin solution.

Preferred embodiments of the present invention seek to overcome one or more of the above disadvantages of the prior art. In particular, preferred embodiments of the present invention seek to reduce the CO loss in processes for the production of formaldehyde.

SUMMARY OF INVENTION

According to the invention a process for the production of formaldehyde from methanol comprises the steps of feeding to a reactor a feed stream comprising the methanol and an oxygen-containing gas; reacting the methanol in the gas phase with the oxygen-containing gas in the reactor in the presence of a catalyst comprising oxides of iron and molybdenum, and recovering a formaldehyde reactor outlet stream comprising formaldehyde and carbon monoxide from the reactor characterised in that the catalyst comprises copper (Cu) in an amount of at least 0.025 wt % of the catalyst, or at least 0.05 wt % of the catalyst.

According to the invention, there is also provided use of a catalyst comprising oxides of iron and molybdenum and copper in an amount of at least 0.025 wt % of the catalyst, or at least 0.05 wt % of the catalyst to reduce CO loss in a process for the production of formaldehyde from methanol. Preferably the process comprises the steps of feeding to a formaldehyde reactor a feed stream comprising the methanol and an oxygen-containing gas; reacting the methanol in the gas phase with the oxygen-containing gas in the reactor in the presence of the catalyst, and recovering a formaldehyde reactor outlet stream from the reactor, the formaldehyde reactor outlet stream comprising formaldehyde and carbon monoxide wherein the CO loss is reduced such that the molar ratio of carbon monoxide to formaldehyde in the formaldehyde reactor outlet stream is, in absolute terms, at least 0.25% less, at least 0.5% less, at least 5% less, at least 7% less, or at least 10% less than the molar ratio of carbon monoxide to formaldehyde in the formaldehyde reactor outlet stream in the same process using a catalyst containing essentially no copper. For example, for a process where the molar ratio of carbon monoxide to formaldehyde in the formaldehyde reactor outlet stream is 5% using a catalyst with essentially no copper, use of the catalyst according to the invention would reduce the molar ratio of carbon monoxide to formaldehyde in the formaldehyde reactor outlet stream to 4.5% or less. In such an example the CO loss is reduced such that the molar ratio of carbon monoxide to formaldehyde in the formaldehyde reactor outlet stream is, in absolute terms, at least 0.5% less than the molar ratio of carbon monoxide to formaldehyde in the formaldehyde reactor outlet stream in the same process using a catalyst containing essentially no copper.

It has also been found that use of a catalyst comprising oxides of iron and molybdenum and copper in an amount of at least 0.025 wt % of the catalyst, or at least 0.05 wt % of the catalyst may reduce methyl formate formation. Preferably the process comprises the steps of feeding to a formaldehyde reactor a feed stream comprising the methanol and an oxygen-containing gas; reacting the methanol in the gas phase with the oxygen-containing gas in the formaldehyde reactor in the presence of the catalyst, and recovering a formaldehyde reactor outlet stream from the formaldehyde reactor, the formaldehyde reactor outlet stream comprising formaldehyde and methyl formate wherein the methyl formate loss is reduced such that the molar ratio of methyl formate to formaldehyde in the formaldehyde reactor outlet stream is, in absolute terms, at least 0.01% less, at least 0.05% less, at least 0.1% less, at least 0.5% less, at least 5% less, at least 7% less, at least 10% less, at least 15% less, or at least 20% less than the molar ratio of methyl formate to formaldehyde in the formaldehyde reactor outlet stream in the same process using a catalyst containing essentially no copper. For example, for a process where the molar ratio of methyl formate to formaldehyde in the formaldehyde reactor outlet stream is 0.10% using a catalyst with essentially no copper, use of the catalyst according to the invention would reduce the molar ratio of methyl formate to formaldehyde in the formaldehyde reactor outlet stream to 0.09% or less; thus the methyl formate loss is reduced such that the molar ratio of methyl formate to formaldehyde in the formaldehyde reactor outlet stream is, in absolute terms, at least 0.01% less than the molar ratio of methyl formate to formaldehyde in the formaldehyde reactor outlet stream in the same process using a catalyst containing essentially no copper.

The reactor may be operated at an inlet pressure suitable to the particular process and the plant equipment available. The skilled person must select an appropriate reactor pressure based on the plant and the desired outcome. A typical process plant for formaldehyde production using a mixed iron-molybdenum oxide catalyst may be operated at a reactor inlet pressure of about 0 barg. 'Barg' indicates gauge pressure in bar, i.e. the pressure above atmospheric pressure. Barg may be converted to bar absolute (bara) by adding the local atmospheric pressure in bar. Using the process of the invention the reactor inlet pressure may be at least 0.4 barg. It is a particular benefit of the process of the invention that the reactor inlet pressure may be increased without increasing, or even while still reducing, the CO loss and/or the methyl formate loss. In other words, because the invention reduces CO loss and/or methyl formate loss compared to prior art processes at the same pressure, a prior art process can have the invention applied and the pressure increased and still maintain the same or better CO loss and/or methyl formate loss. Therefore, the reactor inlet pressure may preferably be at least 0.4 barg, more preferably at least 1.0 barg, yet more preferably greater than 1.5 barg, and even more preferably greater than 3 barg. The reactor inlet pressure may be up to 10 barg or higher than 10 barg.

The oxygen-containing gas may be any suitable gas stream. The concentration of oxygen in the reactor is usually selected by the process designer according to the process which is intended. For example, the oxygen concentration may be selected so that the mixture of oxygen and organic compounds is not explosive. In a typical formaldehyde-producing process, the oxygen-containing gas is air. The oxygen-containing gas may be mixed with the methanol and other components of the feed stream, such as a recycled stream, either within the reactor, at the reactor inlet or before the feed stream is fed through the reactor inlet.

The feed stream may comprise methanol at a concentration of from 1% to 20% by volume of said feed stream. The feed stream may comprise from 3% to 15% by volume of methanol, for example from about 6 vol % to about 12 vol %.

In a typical process the reaction products which leave the reactor which contain some of the product formaldehyde are treated to remove a portion of the product formaldehyde from the formaldehyde reactor outlet stream. This creates a formaldehyde product stream comprising the removed formaldehyde product and a treated stream comprising some formaldehyde along with other by-products such as the carbon monoxide as well as, usually, unreacted methanol, water and dimethyl ether (DME). The other by-products may also comprise nitrogen, for example if the oxygen-containing gas used is air. A portion of the treated stream may be recycled to the reactor. In such a case, the feed stream to the reactor may contain dimethyl ether made as a by-product in the reactor. It is known that when dimethyl ether is added to the reactor, the amount of dimethyl ether made in the reaction tends to be less. The feed stream may for example contain up to about 0.7 vol % of dimethyl ether. Typically the feed stream may contain from about 0.1 to about 0.6 vol % of dimethyl ether. Conversion of methanol to dimethyl ether is a known problem which affects the productivity of formaldehyde processes, particularly when operated at higher inlet pressures. The presence of water in the feed stream to the reactor may reduce the amount of dimethyl ether which is formed. The water may be added as described in WO2016/177999. Preferably sufficient water is added to the feed stream to bring the amount of water in the feed stream to a value in the range of from 3.0 to 15.0 vol % of water, preferably 3.5 to 10.0 vol %.

The catalyst comprises oxides of iron and molybdenum and at least 0.025 wt % copper, or at least 0.05 wt % copper. A typical catalyst used in the oxide process is a mixture of iron molybdate ($Fe_2(MoO_4)_3$) and molybdenum trioxide ($MoO_3$) with a Mo:Fe atomic ratio between 2 and 3, with at least 0.025 wt % copper, or at least 0.05 wt % copper. The copper may be included as the catalyst is produced. For example, when the catalyst is made by precipitation from a solution of soluble iron and molybdenum salts, the copper may be added as a copper salt, such as copper nitrate, copper chloride, copper acetate, copper carbonate or any other copper salt, to the solution. In some methods the copper may be added to a fluid, such as water, used to wash the catalyst post-precipitation. In other methods, the copper can be dissolved in an aqueous solution and added to a dry catalyst powder, before calcination. Upon subsequent calcination of the catalyst, the copper may be converted to an oxide and may form a mixed oxide with the iron and/or the molybdenum or other metal which may be present. The copper may also replace iron or molybdenum, preferably iron, in the ferric molybdate structure to form a doped mixed metal oxide. The copper may be added after the catalyst is produced. For example, the copper may be added to a catalyst by spray drying or impregnation with a solution of a soluble copper salt, such as copper nitrate. The catalyst may then optionally be calcined.

The catalyst may optionally contain oxides of other metals such as vanadium, aluminium, silicon, calcium, cobalt, chromium, magnesium, manganese, nickel, zinc, silver and titanium.

Suitable catalysts may have a specific surface area of about 1-20 $m^2$/g, or 2-20 $m^2$/g, for example 3-10 $m^2$/g. Such catalysts may provide good activity at reasonable manufacturing cost.

The catalyst may take any conventional physical form. Rings, holed cylinders, saddles and spheres are examples of catalyst particle shapes which are known and used in the field. A typical commercial catalyst comprises rings or holed cylinders of outer diameter approximately 4-6 mm and a length approximately 2-5 mm.

The catalyst may comprise an alkali metal or an alkaline earth metal, such as sodium, potassium, magnesium and calcium. Alkali metal (or alkaline earth metal) may be added to the catalyst by any suitable method, for example as described in WO2016/177999.

A conventional catalyst may typically be calcined above 440° C., for example, at 500° C. In order to maintain a good level of activity, the catalyst of the present invention, comprising at least 0.025 wt % copper, or at least 0.05 wt % copper, may have been calcined at not more than 525° C., not more than 500° C., not more than 475° C., not more than 450° C., or not more than 440° C. Preferably the catalyst comprising at least 0.025 wt % copper, or at least 0.05 wt % copper has been calcined at least at 425° C., which may ensure the correct material phases are present. The calcination temperature leaves a detectable difference in the catalyst produced, since the catalyst produced has different, measurable levels of activity and CO loss reduction when the catalyst is calcined at different temperatures. It is common in the art to describe a catalyst by reference to its calcination temperature, rather than trying to describe the physical differences in the catalyst resulting from the different calcination temperatures.

The reaction temperature of the reacting of the methanol in the gas phase with the oxygen-containing gas in the reactor is typically greater than 250° C., normally between 250° C. and 400° C. The reactor feed inlet temperature may typically range from about 60° C. to about 220° C. The reaction temperature may vary along the length of the reactor bed. Normally the reactor is operated such that the temperature is at a maximum at a location between the inlet and the outlet parts of the reactor. The reaction temperature in different parts of the reactor may be affected by the composition of catalyst in the catalyst bed. A mixed catalyst bed may be used, in which a catalyst may be mixed with an inert material or with a catalyst of a different composition and activity to provide a desired activity profile across the catalyst bed. In particular, the catalyst comprising at least 0.025 wt % copper, or at least 0.05 wt % copper may be used in only part of the reactor. The reactor may comprise a catalyst bed, such as in a fixed bed reactor. The reactor will more usually comprise a plurality of parallel catalyst beds, such as in a tubular reactor where a multiplicity of tubes, each containing a catalyst bed, are surrounded by a heat transfer fluid. A tubular reactor may typically comprise hundreds or thousands of such tubes. In preferred embodiments, the downstream third of the catalyst bed or beds may comprise the catalyst comprising at least 0.025 wt % copper, or at least 0.05 wt % copper. The downstream half of the catalyst bed or beds may comprise the catalyst comprising at least 0.025 wt % copper, or at least 0.05 wt % copper. The catalyst comprising at least 0.025 wt % copper, or at least 0.05 wt % copper may be used in the downstream parts of the catalyst bed or beds as that is where most carbon monoxide is formed. In some embodiments, the catalyst comprising at least 0.025 wt % copper, or at least 0.05 wt % copper may be used throughout the catalyst bed or beds or in an upstream part of the catalyst bed or beds. Using the catalyst comprising at least 0.025 wt % copper, or at least 0.05 wt % copper in only part of the catalyst bed or beds may be particularly advantageous if the activity of the catalyst comprising at least 0.025 wt % copper, or at least 0.05 wt % copper differs from the activity of the standard prior art catalysts.

The reaction temperature may be controlled by means of a heat transfer system. The reactor temperature may be varied over time. A typical catalyst tends to lose activity over its useful lifetime. The reactor temperature may be varied to take account of such a loss in activity.

The catalyst comprises copper in an amount of at least 0.025 wt % copper, or at least 0.05 wt % copper of the catalyst. Preferably the catalyst comprises copper in an amount of at least 0.025 wt % of the catalyst; at least 0.05 wt % of the catalyst; at least 0.075 wt % of the catalyst, at least 0.1 wt % of the catalyst, more preferably at least 0.15 wt % of the catalyst. The catalyst may comprise copper in an amount of at least 1 wt % of the catalyst. In some embodiments, the catalyst may comprise copper in an amount of not more than 2 wt % of the catalyst, or not more than 10 wt % of the catalyst, or not more than 15 wt % of the catalyst, or not more than 20 wt % of the catalyst.

Preferably the molar ratio of carbon monoxide to formaldehyde in the formaldehyde reactor outlet stream is less than 6%, less than 5%, less than 4%, less than 3%, less than 2% or less than 1.5%.

Preferably the process produces at least 7.4 MTPD, at least 500 MTPD, or at least 1,000 MTPD of formaldehyde. The formaldehyde is preferably produced as at least 20 MPTD 37 wt % formaldehyde solution in water.

It will be appreciated that features described in relation to one aspect of the invention may be equally applicable in another aspect of the invention. For example, features described in relation to the process of the invention, may be equally applicable to the use of the invention, and vice versa. Some features may not be applicable to, and may be excluded from, particular aspects of the invention.

DESCRIPTION OF THE DRAWINGS

Embodiments of the present invention will now be described, by way of example, and not in any limitative sense, with reference to the accompanying drawings, of which.

DETAILED DESCRIPTION

Figure 1:
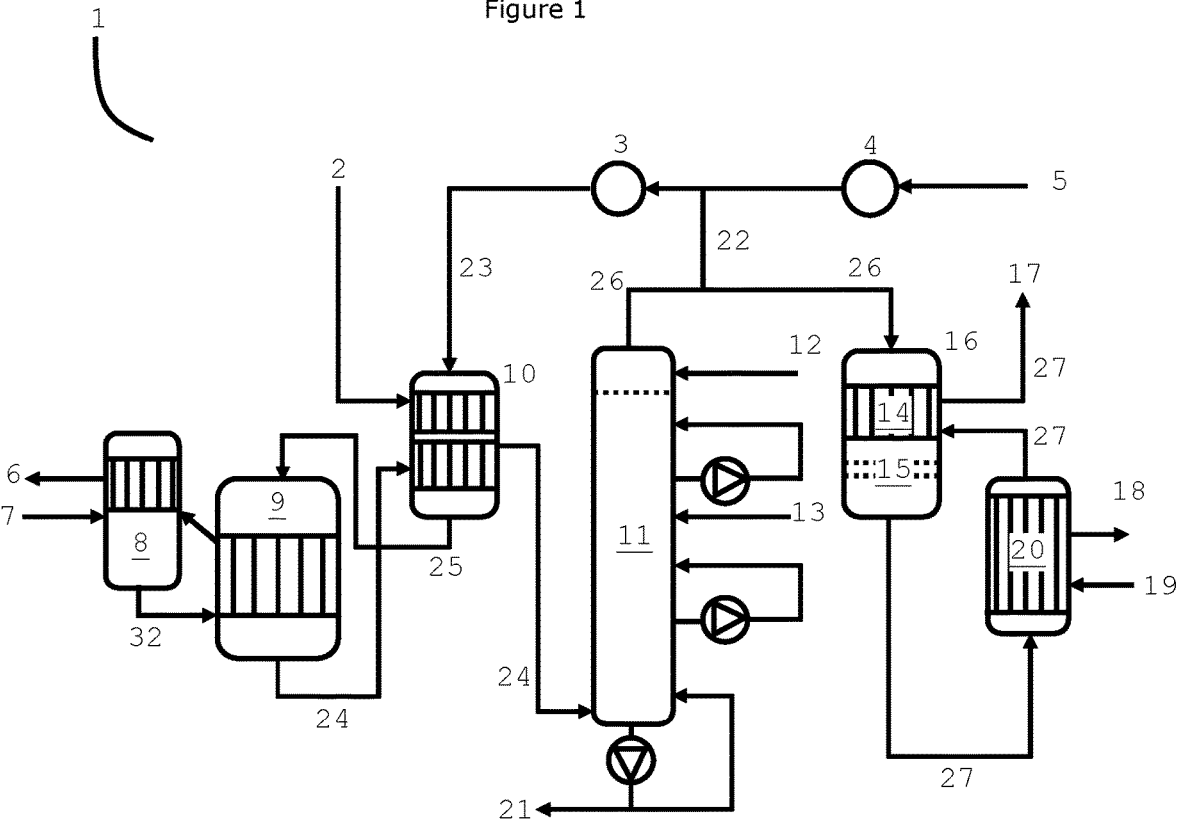
FIG. 1 is a schematic of a process for the production of formaldehyde.

Formaldehyde can be produced by the catalytic oxidative dehydrogenation of methanol. Processes for carrying out such production are known, for example from WO9632189 or U.S. Pat. No. 2,504,402. A well-known process for the production of formaldehyde is the Formox process offered by Johnson Matthey. The Formox process is illustrated schematically in FIG. 1. In the illustrated Formox process 1a fresh air stream 5 is passed through a pressurisation blower 4 and then mixed with a recirculation stream 22 to form a mixed stream 23 before being fed via a recirculation blower 3 to a vaporiser 10. In the vaporiser 10, the mixed stream 23 is mixed with a methanol stream 2 and vaporised using heat from a formaldehyde reactor outlet stream 24 leaving a reactor 9. The resulting feed stream 25 is fed to the reactor 9 which, in this embodiment, is an isothermal reactor cooled by vaporisation of a heat transfer fluid 32. The heat transfer fluid 32 passes to a condenser 8, where it is condensed and steam 6 generated from boiler feed water 7, before returning to the reactor 9. In the reactor 9, the methanol in the feed stream 25 reacts on catalyst beds to produce formaldehyde, which exits the reactor 9 in a formaldehyde reactor outlet stream 24 comprising the formaldehyde, carbon monoxide produced as a by-product, water, other by-products (such as dimethyl ether, methyl formate, carbon dioxide, and/or dimethoxymethane), and unreacted parts of the feed stream 25. In processes according to the present invention, the catalyst beds comprises catalyst comprising at least 0.025 wt % copper, or at least 0.05 wt % copper, and the molar ratio of carbon monoxide to formaldehyde in the formaldehyde reactor outlet stream 24 is preferably less than 6%, less than 5%, less than 4%, or less than 3%. The formaldehyde reactor outlet stream 24 passes through the vaporiser 10, where heat in the formaldehyde reactor outlet stream 24 is used to vaporise the feed stream 25, and is fed to an absorber 11. In the absorber 11, process water 12 and optionally urea 13 flows down and strips the formaldehyde from the process stream 24 flowing up the absorber 11. The water 12, and optionally urea 13, together with the formaldehyde exits the bottom of the absorber as a product stream 21. That product stream 21 is typically 55% formalin, if just process water 12 is used, or UFC if urea 13 is used. The remainder of the formaldehyde reactor outlet stream 24 exits the top of the absorber as a waste gas stream 26. That waste gas stream 26 is partially recycled as the recirculation stream 22 and the remainder is sent to an emissions control system 16. In the emissions control system 16, the waste gas stream 26 is first heated in a pre-heater 14 using energy from the combusted waste gas stream 27 leaving the emissions control system 16 and then combusted in a catalyst bed 15 having a catalyst comprising structured or supported Pd on $Al_2O_3$ and/or Pt on $Al_2O_3$ to form the combusted waste gas stream 27. The combusted waste gas stream 27 leaving the catalyst bed 15 has a temperature of around 500° C. to 540° C. and is fed to a steam generator 20, where the combusted waste gas stream 27 is cooled and boiler feed water 19 is turned into steam 18, and then fed back to the pre-heater 14 of the emissions control system 16 to heat the incoming waste gas stream 26. The combusted waste gas stream 27 leaving the pre-heater 16 is sent to a stack 17.

It will be appreciated by persons skilled in the art that the above embodiments have been described by way of example only, and not in any limitative sense, and that various alterations and modifications are possible without departure from the scope of the invention as defined by the appended claims.

EXAMPLES

Example 1

The following catalyst samples were prepared using the method described below.

A—Iron Molybdate sol-gel

B—Iron Molybdate with 0.64 wt % Al (10 mol % Fe content of 'A' substituted for Al).

C—Iron Molybdate with 1.5 wt % Cu (10 mol % Fe content of 'A' substituted for Cu).

D—Iron Molybdate with 1.54 wt % Zn (10 mol % Fe content of 'A' substituted for Zn).

E—Iron Molybdate with 1.3 wt % Mn (10 mol % Fe content of 'A' substituted for Mn).

F—Iron Molybdate with 0.32 wt % Al (5 mol % Fe content of 'A' substituted for Al).

G—Iron Molybdate with 0.75 wt % Cu (5 mol % Fe content of 'A' substituted for Cu).

H—Iron Molybdate sol-gel with 0.38 wt % Cu (2.5 mol % Fe content of 'A' substituted for Cu).

I—Iron Molybdate sol-gel repeat of A

Samples A and I were prepared as follows. 7.5 g iron nitrate nonahydrate was dissolved in 100 mL $H_2O$ and 10 g citric acid was added. A solution of 7.54 g ammonium paramolybdate in 100 mL was then added and the solution dried on a hotplate at 80° C. until a glassy texture was observed. Drying was completed in a vacuum oven overnight at 70° C. The resulting glassy material is broken up with a pestle and mortar and then calcined. The calcination procedure is as follows: 2° C./min to 230° C., hold for 30 minutes, 10° C./min to 350° C., hold for 1 minute, 2° C./min to 450° C., hold for 30 minutes, 10° C./min to 500° C. hold for 2 hours, 20° C./min cool to room temperature.

Samples B, C, D and E were prepared as above, except that 6.7484 g of iron nitrate nonahydrate was mixed with the following:

B—0.6962 g aluminium nitrate nonahydrate

C—0.4317 g copper nitrate hemi-pentahydrate

D—0.4852 g zinc nitrate tetrahydrate

E—0.4658 g manganese nitrate tetrahydrate Samples F and G were prepared as above for samples A and I, except that 7.125 g of iron nitrate was mixed with:

F—0.3482 g aluminium nitrate nonahydrate

G—0.2159 g copper nitrate hemipentahydrate

Sample H was prepared as above for samples A and I, except that 7.3515 g iron nitrate was mixed with 0.1079 g copper nitrate hemipentahydrate All catalyst samples were granulated to 250-470 microns for testing and blended with silicon carbide (450 mg SiC per 100 mg catalyst) with a 300 mg SiC layer on top of the bed. For several catalysts the catalyst loading was varied in order to achieve different conversions and enable comparison of catalysts at the same conversion (particularly when comparing to the reference iron molybdenum only catalyst).

Testing was carried out in a 5 mm ID stainless steel reactor, with the reactor set to 310° C. A stream of methanol-water-formaldehyde was passed over the catalyst with the products analysed using a GC. The composition of the gas stream was as follows:

90 mL/min air 90 mL/min helium 40 mL/min nitrogen

38 μL/min liquid pump rate

This gave an oxygen content of approximately 7.38%, a methanol concentration of approximately 4.9%, water at approximately 5.7% and formaldehyde at approximately 2.2%. The precise methanol concentration was determined by sampling through the reactor bypass run at the start of each experiment and, after adjusting for reactor conversion, the performance of the catalyst was determined.

Figure 2:
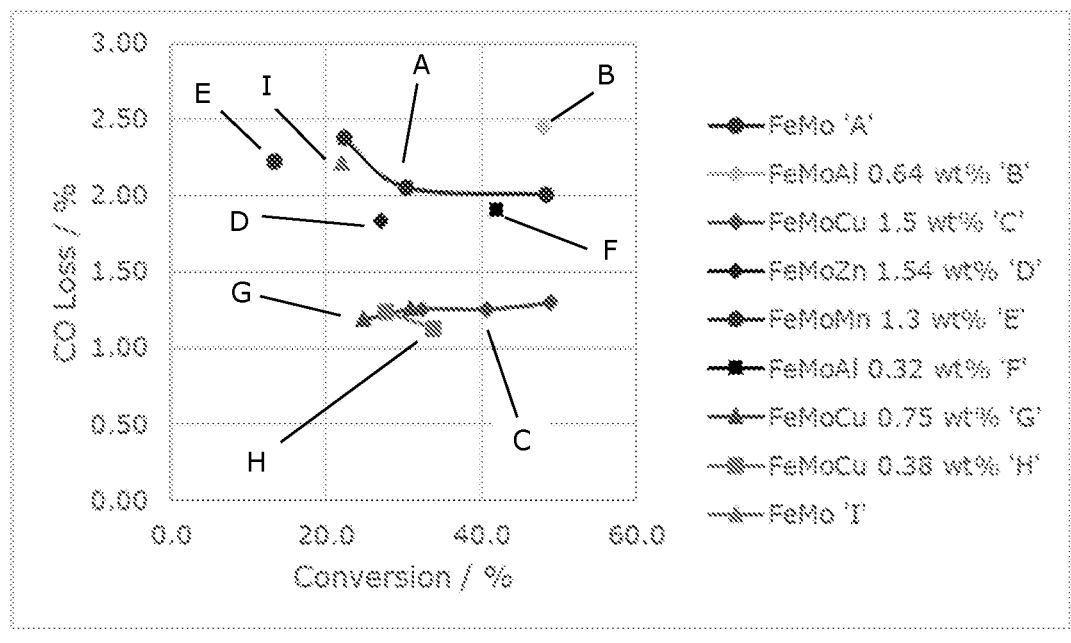
FIG. 2 is a graph of CO loss against conversion for various catalyst samples.

Results from methanol oxidation testing are summarised in FIG. 2. The data points are labelled with the catalyst sample letter.

The results show that copper addition, at a range of loadings, leads to a consistently lower CO loss when compared to an equivalent iron-molybdenum oxide only catalyst.

The CO loss is reduced by approximately 0.75% in absolute terms. The other metals are less effective, aluminium has little effect at 5% substitution and increases CO loss at 10%. Zinc leads to a slight reduction in CO loss, while manganese substantially reduces catalyst activity and could not achieve conversion comparable to the standard catalysts.

The addition of copper thus shows a surprising reduction in the CO loss both compared to standard catalysts and compared to the addition of other metals.

Example 2

A further test was carried out in which the catalyst samples were prepared by precipitation rather than the sol-gel method. Precipitation is more commonly used for the commercial production of prior art catalysts. In this example, copper is added to the catalyst washing water post-precipitation and the iron content is not reduced to account for the addition of copper.

A precipitate ('FeMo') was prepared according to Soederhjelm, et al., "On the Synergy Effect in $MoO_3$—$Fe_2(MoO_4)_3$ Catalysts for Methanol Oxidation to Formaldehyde," Top Catal (2008) 50:145-155.

Following addition, the precipitate was aged for 2 hours at 60° C., before being filtered, washed with 250 mL distilled water, and filtered again.

After the fourth filtration, the solids content of the filter cake was determined, the filter cake was weighed, and the amount of catalyst present was determined based on the total mass, solids content, and accounting for 10% mass loss on calcination. The amount of copper (II) nitrate hemipentahydrate added to the catalyst was for each sample was:

Sample J—FeMo+Cu (0.0052 g Cu-nitrate per g catalyst)

Sample K—FeMo+Cu (0.0260 g Cu-nitrate per g catalyst)

Sample L—FeMo+Cu (0.0520 g Cu-nitrate per g catalyst)

Sample M—FeMo+Cu (0.00904 g Cu-nitrate per g catalyst)

Sample N: FeMo+Cu (0.0025 g Cu-nitrate per g catalyst)

Sample O: FeMo+Cu (0.0013 g Cu-nitrate per g catalyst)

Sample P: FeMo+Cu (0.0071 g Cu-nitrate per g catalyst)

The Cu was added in the form of a Cu-nitrate solution by dispersing the filter cake in the solution and then filtering.

The Cu-containing filter cake was recovered, dried at 100° C. overnight and then calcined at 500° C. for 2 hours (10° C./min ramp up and down).

Reference sample Q was prepared in the same way, except that no copper (II) nitrate was added.

Catalysts were granulated to 250-470 microns for testing and blended with silicon carbide (450 mg SiC per 100 mg catalyst) with a 300 mg SiC layer on top of the bed. For several catalysts the catalyst loading was varied in order to achieve different conversions and enable comparison of catalysts at the same conversion (particularly when comparing to the reference iron molybdenum only catalyst).

Testing was carried out in a 5 mm ID stainless steel reactor, with the reactor set to 310° C. A stream of methanol-water-formaldehyde was passed over the catalyst with the products analysed using a GC. The composition of the gas stream was as follows:

90 mL/min air 90 mL/min helium 40 mL/min nitrogen

38 μL/min liquid pump rate

This gave an oxygen content of approximately 7.38%, a methanol concentration of approximately. 4.9%, water at approximately 5.7% and formaldehyde at approximately 2.2%. The precise methanol concentration was determined by sampling through the reactor bypass run at the start of each experiment and, after adjusting for reactor conversion, the performance of the catalyst was determined.

ICP results are shown below:

| Sample | Mo/wt % | Fe/wt % | Cu/wt % |
|---|---|---|---|
| J | 53.1 | 14 | 0.11 |
| K | 52.9 | 14.3 | 0.32 |
| L | 52.5 | 14.3 | 0.51 |
| M | 53.1 | 14.6 | 0.21 |
| N | 53.4 | 14.6 | 0.07 |
| O | 52.8 | 14.7 | 0.04 |
| P | 52.6 | 14.7 | 0.18 |
| Q | 53.4 | 13.8 | 0 |

BET surface area measurements were performed on the samples:

| Sample | BET Surface Area (m2/g) |
|---|---|
| J | 10.21 |
| K | 9.9 |
| L | 10.08 |
| M | 9.61 |
| N | 11.04 |

-continued

| Sample | BET Surface Area (m2/g) |
|---|---|
| O | 11.06 |
| P | 10.49 |
| Q | 10.55 |

Figure 3:
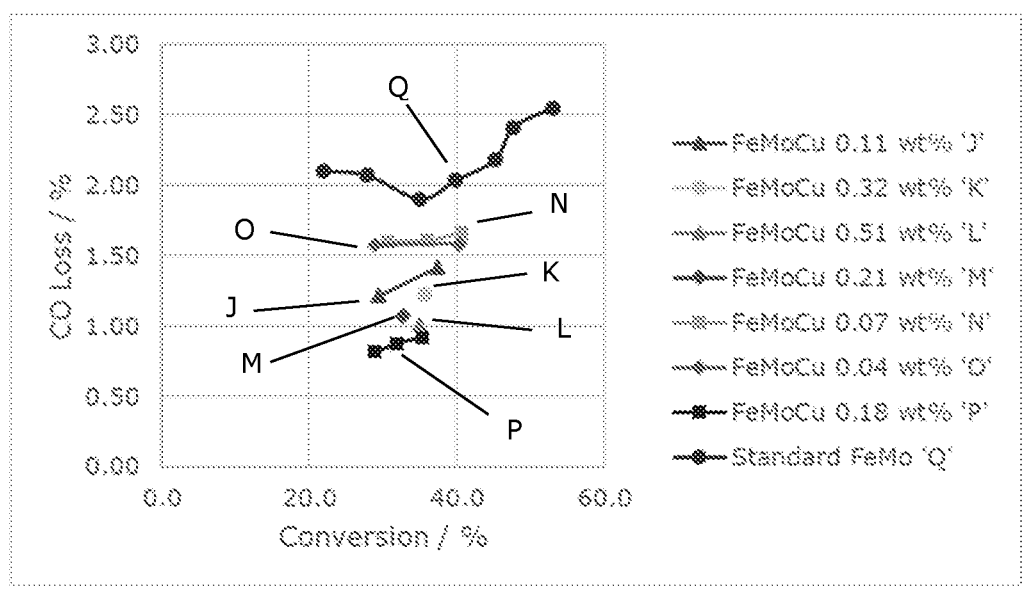
FIG. 3 is a graph of CO loss against conversion for various catalyst samples.
Figure 4:
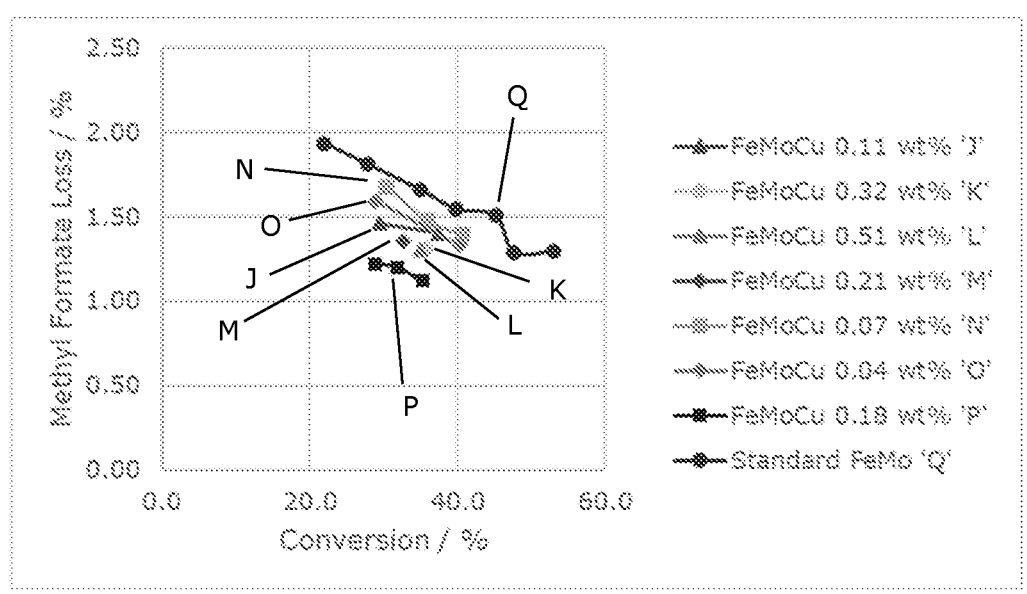
FIG. 4 is a graph of methyl formate loss against conversion for various catalyst samples.

Catalyst testing results for the samples are illustrated in FIGS. 3 and 4 and show a marked reduction in CO loss and methyl formate loss, respectively for the catalysts where copper was added. Results show CO loss is around 1% lower and the methyl formate loss was 0.4% lower, in absolute terms, for the copper containing catalysts, although catalyst activity was diminished at ~2.14 μmol m$^{-2}$s$^{-1}$ compared to ~2.65 μmol m$^{-2}$s$^{-1}$ for the copper free catalyst. Note the catalysts are tested over the same conversion ranges making the results comparable.

Example 3

A further test was carried out in which the catalyst preparation of example 2 was scaled up (sample S). 1 kg of catalyst was prepared using precipitation, and then washed, and filtered. The filter cake was dispersed solution, and copper was added in the form of a Cu-nitrate solution. The Cu-containing filter cake was recovered, dried at 100° C. overnight.

The Cu-containing filter cake was blended with tabletting aids, pre-compacted, granulated and pelleted using a single-punch tabletting machine. The tablets were formed as Raschig rings with dimensions of 5.0 mm (outer diameter), 2.7 mm (inner diameter) and 2.7 mm (height) post calcination.

The tablets were calcined at 473° C. for 4 hours.

The XRF and BET surface area results are shown below:

| Sample | Elemental composition (XRF) | | | BET Surface Area (m2/g) |
|---|---|---|---|---|
| | Mo/wt % | Fe/wt % | Cu/wt % | |
| Sample S | 53.39 | 13.60 | 0.07 | 5.9 |

Testing was carried out on a pilot plant in a 21 mm ID stainless steel reactor using a Johnson Matthey standard loading plan, with reactor heated to 267° C. using a HTF system. The pressure at the reactor inlet was set to 1.68 barg. A stream of methanol-water was passed over the catalyst with the products analysed using a GC. The gas consisted of approximately 10.0% methanol, 2.7% water, 9.6% oxygen and 77.7% nitrogen. The total flow was 66.9 Nl/min.

Figure 5:
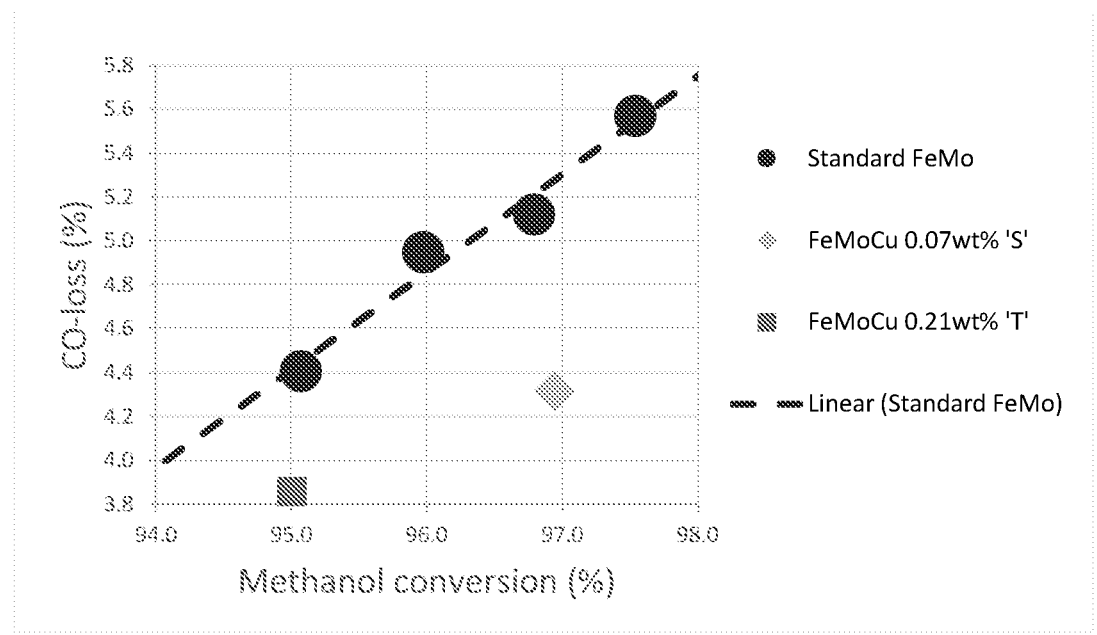
FIG. 5 is a graph of CO loss against conversion for samples S and T.

Sample S was compared to a commercial reference catalyst ("standard FeMo"). See also FIG. 5:

| Sample | MeOH conversion (%) | Yield (%) | | | | |
|---|---|---|---|---|---|---|
| | | FA | CO | DME | MF | DMM |
| Standard FeMo | 97.04 | 88.19 | 5.17 | 3.14 | 0.19 | 0.11 |
| Sample S | 96.94 | 88.90 | 4.32 | 3.28 | 0.16 | 0.03 |

Example 4

A pilot scale test was carried out using a copper containing catalyst which was prepared by an incipient wetness impregnation technique (sample T). Here, the preparation follows that in example 3, in that the precipitation, washing and filtration steps are the same. After drying at 110° C. for 24 h, the powder, having <3% moisture content was dispersed in a crystallisation dish. Then, an aqueous copper solution (copper chloride, 0.21 wt % for final dried catalyst) was poured over the top of the dry powder. After air drying at ambient conditions, the powder was then dried at 110° C. for 24 h again.

The Cu-containing powder was blended with tabletting aids, pre-compacted, granulated and pelleted using a single-punch tableting machine. The tablets were formed as Raschig rings with dimensions of 5.0 mm (outer diameter), 2.7 mm (inner diameter) and 2.7 mm (height) post calcination.

The tablets were calcined at 460° C. for 4 hours.

The XRF and BET surface area results are shown below:

| | Elemental composition (XRF) | | | BET Surface Area |
|---|---|---|---|---|
| Sample | Mo/wt % | Fe/wt % | Cu/wt % | (m2/g) |
| Sample T | 53.08 | 13.71 | 0.21 | 6.5 |

Testing was carried out on a pilot plant in a 21 mm ID stainless steel reactor using a Johnson Matthey standard loading plan, with reactor heated to 267° C. using a HTF system. The pressure at the reactor inlet was set to 1.68 barg. A stream of methanol-water was passed over the catalyst with the products analysed using a GC. The gas consisted of approximately 10.0% methanol, 2.7% water, 9.6% oxygen and 77.7% nitrogen. The total flow was 66.9 Nl/min.

Sample T was compared to a commercial reference catalyst ("standard FeMo"). See also FIG. 5:

| | MeOH | Yield (%) | | | | |
|---|---|---|---|---|---|---|
| Sample | conversion (%) | FA | CO | DME | MF | DMM |
| Standard FeMo | 97.04 | 88.19 | 5.17 | 3.14 | 0.19 | 0.11 |
| Sample T | 94.99 | 84.66 | 3.86 | 3.45 | 0.29 | 2.52 |

The invention claimed is:

1. A process for the production of formaldehyde from methanol comprising the steps of:

feeding to a reactor a feed stream comprising the methanol and an oxygen-containing gas;

reacting the methanol in the gas phase with the oxygen-containing gas in the reactor in the presence of a catalyst comprising oxides of iron and molybdenum and copper in an amount of at least 0.025 wt % of the catalyst; and recovering a formaldehyde reactor outlet stream from the reactor, the formaldehyde reactor outlet stream comprising formaldehyde and carbon monoxide, wherein the CO loss is reduced such that the molar ratio of carbon monoxide to formaldehyde in the formaldehyde reactor outlet stream is at least 0.25% less than the molar ratio of carbon monoxide to formaldehyde in the formaldehyde reactor outlet stream in the same process using a catalyst containing essentially no copper.

2. A process for the production of formaldehyde from methanol comprising the steps of:

feeding to a reactor a feed stream comprising the methanol and an oxygen-containing gas;

reacting the methanol in the gas phase with the oxygen-containing gas in the reactor in the presence of a catalyst comprising oxides of iron and molybdenum; and recovering a formaldehyde reactor outlet stream comprising formaldehyde and carbon monoxide from the reactor;

wherein the catalyst comprises copper in an amount of at least 0.025 wt % of the catalyst.

3. A process for the production of formaldehyde from methanol comprising the steps of:

feeding to a reactor a feed stream comprising the methanol and an oxygen-containing gas;

reacting the methanol in the gas phase with the oxygen-containing gas in the reactor in the presence of a catalyst comprising oxides of iron and molybdenum and copper in an amount of at least 0.025 wt % of the catalyst; and recovering a formaldehyde reactor outlet stream from the reactor, the formaldehyde reactor outlet stream comprising formaldehyde and carbon monoxide, wherein the methyl formate loss is reduced such that the molar ratio of methyl formate to formaldehyde in the formaldehyde reactor outlet stream is at least 0.01% less than the molar ratio of methyl formate to formaldehyde in the formaldehyde reactor outlet stream in the same process using a catalyst containing essentially no copper.

4. The process according to claim 1, wherein the catalyst comprises copper in an amount of at least 0.05 wt % of the catalyst.

5. The process according to claim 1, wherein the reactor is operated at an inlet pressure of at least 1 barg.

6. The process according to claim 1, wherein said oxygen-containing gas is air.

7. The process according to claim 1, wherein the catalyst has been calcined at a temperature of not more than 525° C.

8. The process according to claim 7, wherein the catalyst has been calcined at a temperature of at least 425° C.

9. The process according to claim 2, wherein the catalyst comprises copper in an amount of at least 0.05 wt % of the catalyst.

10. The process according to claim 2, wherein the reactor is operated at an inlet pressure of at least 1 barg.

11. The process according to claim 2, wherein said oxygen-containing gas is air.

12. The process according to claim 2, wherein the catalyst has been calcined at a temperature of not more than 525° C.

13. The process according to claim 11, wherein the catalyst has been calcined at a temperature of at least 425° C.

14. The process according to claim 3, wherein the catalyst comprises copper in an amount of at least 0.05 wt % of the catalyst.

15. The process according to claim 3, wherein the reactor is operated at an inlet pressure of at least 1 barg.

16. The process according to claim 3, wherein said oxygen-containing gas is air.

17. The process according to claim 3, wherein the catalyst has been calcined at a temperature of not more than 525° C.

18. The process according to claim 16, wherein the catalyst has been calcined at a temperature of at least 425° C.

* * * * *